SUGAR CANE
Filed Oct. 4, 1965 4 Sheets-Sheet 1
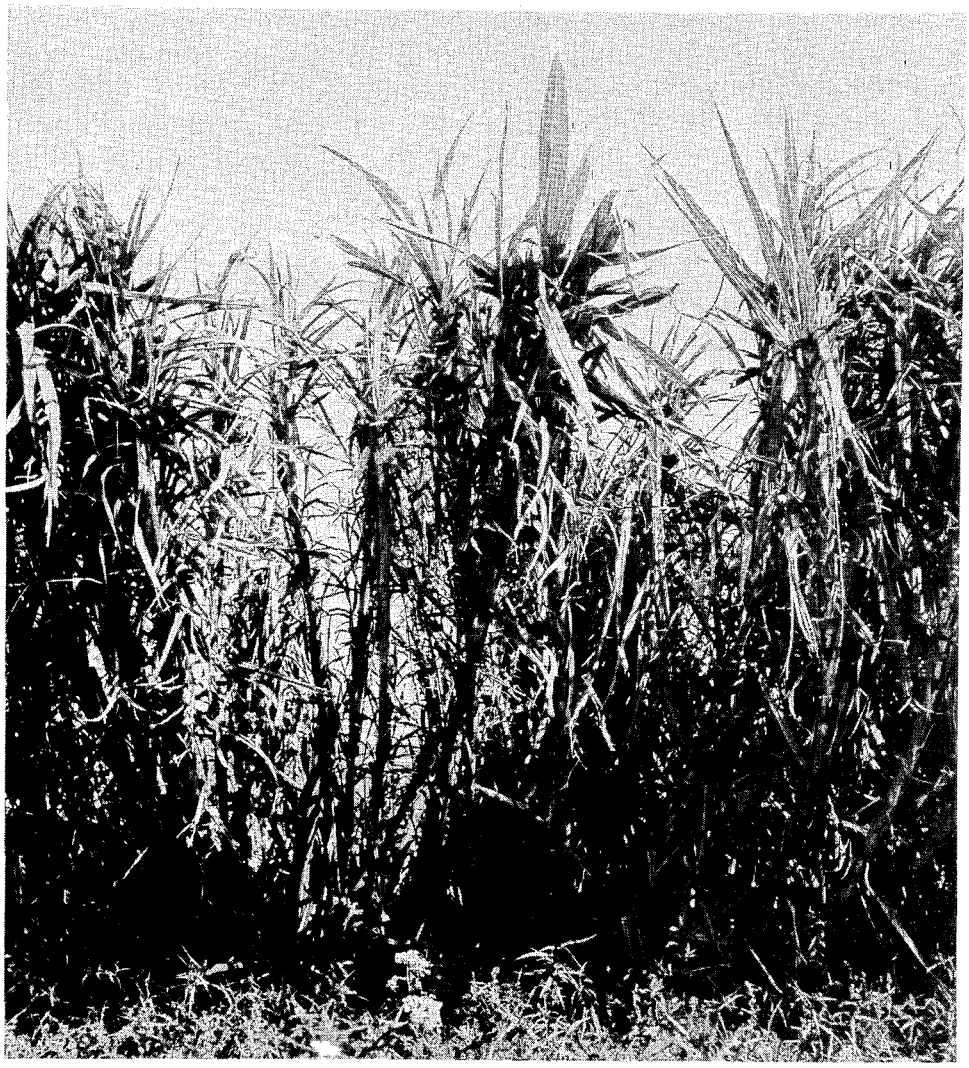
FIG. I
INVENTORS
LESLIE M. WEETMAN
BENJAMIN A. BOURNE
BY
Cushman, Darby & Cushman
ATTORNEYS

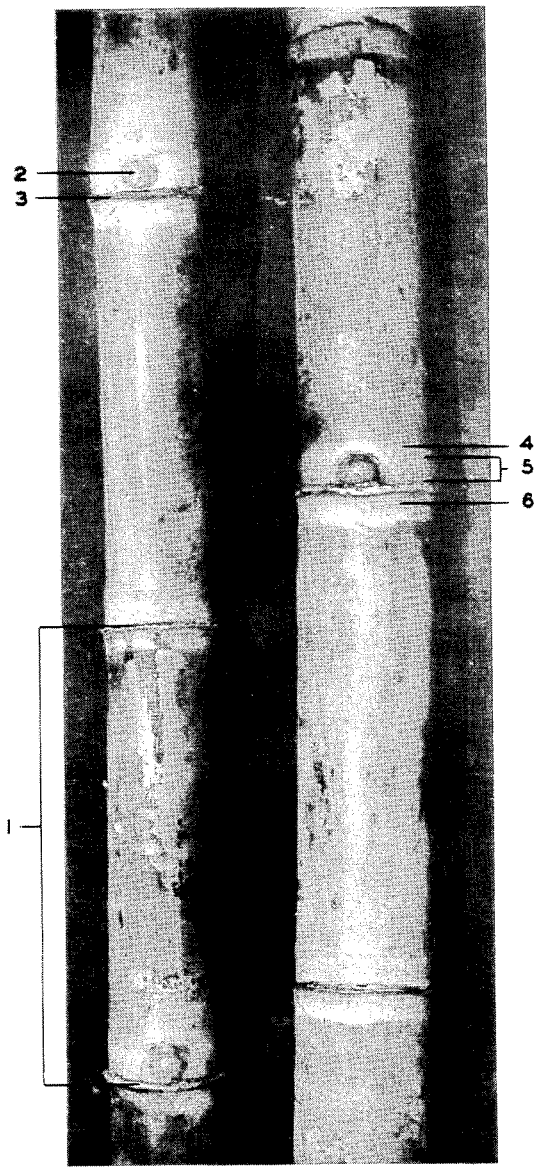
FIG. II
INVENTORS
LESLIE M. WEETMAN
BENJAMIN A. BOURNE
BY
Cushman, Darby & Cushman
ATTORNEYS SUGAR CANE
Filed Oct. 4, 1965 4 Sheets-Sheet 3
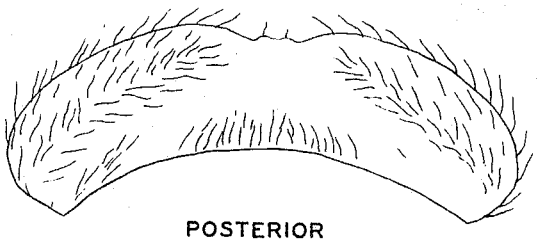
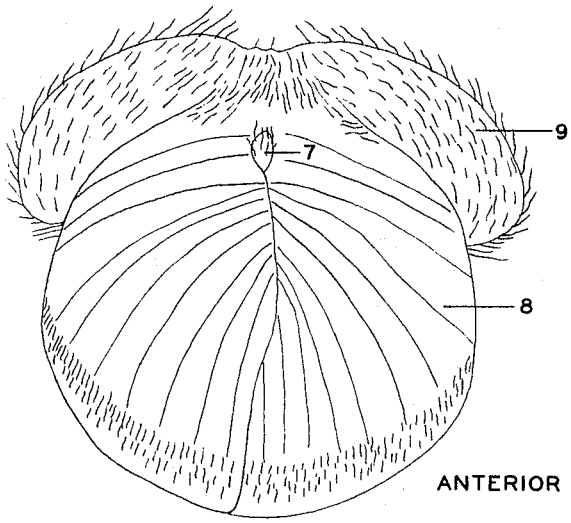
FIG. III
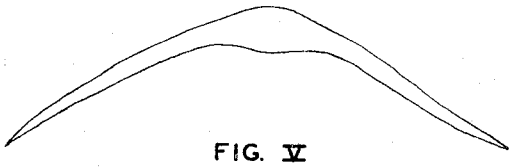
FIG. V
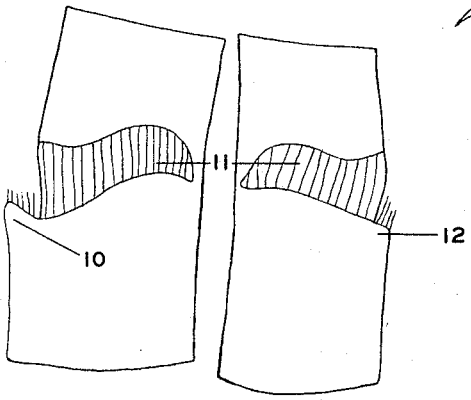
FIG. IV
INVENTORS
LESLIE M WEETMAN
BY BENJAMIN A. BOURNE
Cushman, Darby & Cushman
ATTORNEYS

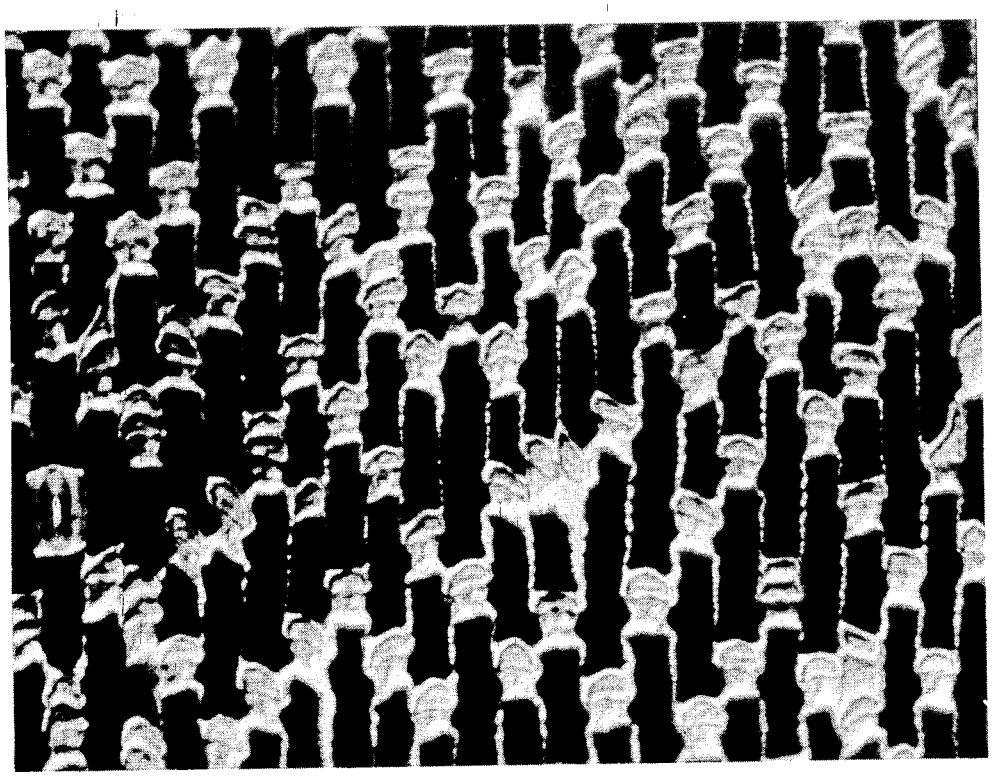
FIG. VI
INVENTORS
LESLIE M. WEETMAN
BY BENJAMIN A. BOURNE
Cushman, Darby & Cushman
ATTORNEYS United States Patent Office Plant Pat. 2,715
Patented Feb. 14, 1967

2,715
SUGAR CANE

Leslie M. Weetman and Benjamin A. Bourne, both of Clewiston, Fla., assignors to United States Sugar Corporation, Clewiston, Fla., a corporation of Delaware Filed Oct. 4, 1965, Ser. No. 494,303
1 Claim. (Cl. Plt.—89)

This new variety of sugar cane originated as a seedling produced by the inventors by crossing the variety F. 36–819 as female and the variety Cl. 47–83 as male. (In this form of variety designation, which is well known to sugar cane breeders, "Cl." denotes the breeding locality or station, i.e., Clewiston, Florida; "47" represents the year that the particular variety was first grown, i.e., 1947; and "83" is the distinctive number assigned to that variety among those grown in that year.) The cross was made in January 1954, at Clewiston, Florida, and this new variety was selected from among the progeny of the cross. The inventors have subsequently propagated the variety at Clewiston, Florida, by means of stem cuttings under the identifying number Cl. 54–405.

In a replicated trial extending over three crop years, juice analyses were made in mid-November and again in January or February each year. Average indicated yields of 96° sugar per ton of cane were 225 pounds for the November analyses and 253 pounds for the January-February analyses, indicating medium early maturity and attainment of very high sucrose content for late harvest. This variety is also vigorous and produces a high tonnage of cane per acre.

Our new variety was planted on cold marginal land, consisting of typical low-mineral organic Everglades peat, in August 1962. In the following mid-December and toward mid-January, it was subjected to below-freezing temperatures on several successive days whereby all above-ground parts of the cane were killed. Subsequently the variety grew up again to a perfect stand and with good vigor and stooling, indicating that it is resistant to winter killing.

This variety has been under exposure to natural infection by all four strains of mosaic disease virus known in Florida, viz: A, B, D and E (atypical) for several years and none of the plants has become infected. However, in preliminary tests with an extracted mixture of all four of the above virus strains using a high pressure spray gun for inoculation at 130–140 p.s.i., it was found possible to infect four out of four plants. Further inoculation tests using 21 plants in each case have been carried out using the same mixture of the four virus strains and the high pressure air gun and these have shown 95.2 percentage of infection. In addition, 20 plants were exposed to the corn viruliferous vector *Rhopalosiphum maidis* Fitch, after these insects had been allowed to feed on artifically infected sorghum plants inoculated with the four-strain mixture from sugar cane. In these tests the variety became 30.0 percent infected.

Because mosaic disease virus existing in Florida only in isolated areas for the most part can be transmitted to our new variety by means of the insect vector *Rhopalosiphum maidis* Fitch, from artificially infected sorghum plants under very favorable conditions, it is suggested that commercial plantings be as far removed from fields of sorghum as possible and that seedcane plots be inspected and rogued of any diseased plants present as a means of providing adequate control of this virus.

In view of the importance of the ratoon stunting virus (RSD) in reducing the yields of susceptible varieties, this variety was tested during a complete crop cycle of 19 months duration in 1/50 acre plots replicated five times in a randomized block experiment. Five plots were planted with seedcane obtained from a propagation plot established with stalks heat treated at 50° C. for 24 hours (hot air) in order to eliminate any possible RSD virus present and five similar plots were planted with seedcane previously unheated and inoculated by immersion of freshly cut cuttings in newly expressed stalk juice of a severely infected variety. It was found that the heat treated cane plots were significantly lower in percent yield of 96° sugar by 0.52 point, shortly after the middle of November, but this effect on cane quality early in the harvest season disappeared by late January. On the average, the disease-free plots yielded 4.49 tons cane and 0.63 ton 96° sugar per acre more than the diseased ones by late January. However, these yield differences failed to be significant at the 5% level, although in yield of 96° sugar per acre the increase reached the border line of significance. As a result of these field tests, it has been shown that the variety is moderately susceptible to the RSD virus. If non-heated, disease-free plants cannot be secured for cultivation, then it is recommended that RSD virus free propagation plots be established for commercial use by heat treating stalks at 50° C. for 24 hours in hot air. In the case of heat treated cane as above, harvesting should be delayed until late December or longer, in order to overcome the adverse effect of the heat treatment on cane quality.

Comparative replicated test plots of this new variety growing on low mineral organic soil approximately 6½ miles south of the cold protection influence of Lake Okeechobee, Fla., showed that it was quite resistant to both the brown stripe disease caused by *Helminthosporium stenospilum* Drechs. and also pokkah boeng disease caused by *Gibberella moniliformis* (Sheldon) Wineland. Control canes were the released varieties C.P. 50–28, Cl. 41–223 and F. 46–136, all of which are of commercial importance in Florida and show susceptibility to brown stripe but good resistance to pokkah boeng. Since the above two fungus diseases are responsible for serious losses in sugar cane yields when a variety is susceptible to either one or both of them, the dual resistance of our new variety represents a marked improvement of significant importance to the industry.

In the drawings:

FIGURE I is a photographic view showing the habit of growth of mature cane;

FIGURE II is a photographic view of approximate midsections of typical stalks, showing internode 1, stem bud 2, leaf scar 3, growth ring 4, root band 5, and wax ring 6;

FIGURE III shows anterior and posterior views of the prophyll (or outermost bud scale) of the stem bud, showing germ pore 7, central disk 8, and wing 9;

FIGURE IV is a view of the two separated and flattened halves of the upper part of a leaf sheath, showing the inner auricle 10, the dewlap or blade joint 11, and the outer auricle 12;

FIGURE V is a view showing the outline of a ligule after its removal from the inner surface of the leaf sheath; and FIGURE VI is a photomicrographic view showing the pattern of the stem epidermal cells.

DETAILED DESCRIPTION

In the following detailed description of the new variety of sugar cane, the terminology employed in morphological description and numbering of hair groups is that employed by Artschwager (see Sugarcane (*Saccharum officinarum* L.): Origin, Classification, Characteristics, and Description of Representative Clones by Ernst Artschwager and E. W. Brandes. Agriculture Handbook No. 122. United States Department of Agriculture, 1958). Color descriptions are made by referring to the plates of Maerz and Paul (see A dictionary of Color, second edition, by A. Maerz and M. Rea Paul. McGraw-Hill Book Company, 1950).

*The stalk (or culm)*

*Habit of growth* (see FIGURE I).—The stalks are at first erect, and in some years they remain erect, but sometimes they become semi-recumbent by maturity. The internodes show a slight zig-zag alignment.

*Size.*—The stalks are generally 8 or 9 or more feet long in mature plant cane. They are nearly circular in cross-section, averaging 32.2 x 33.1 millimeters in the middle part of the stalk. The larger diameter may vary from 29 to 40 millimeters.

*Flesh.*—The color of the flesh is approximately Maerz and Paul's designation 11–H–2. The flesh is solid and contains a low percent fiber.

*Internodes* (1, FIGURE II).—They are cylindrical or slightly concave-convex in shape and vary from 10 to 14 centimeters in length in the middle parts of the stalks, averaging 12.2 centimeters. Usually there are no bud furrows; however, very shallow furrows appear occasionally on older internodes. Corky cracks and growth cracks are not evident.

*Color.*—The basic rind color just above the growth ring on young unexposed internodes is approximately Maerz and Paul's 19–F–1. Upper parts of the internodes are more greenish, usually with streaks of pink or red, and are coated with a whitish layer of wax. Older internodes become splotched with black mold, and exposed portions turn red. The wax ring (6, FIGURE II) is moderately heavy and is distinctly demarcated.

*Growth ring* (4, FIGURE II).—It is 1 to 2 millimeters in height and slightly tumescent. The color is more olive than the intermode and turns green with exposure to the sun.

*Root band* (5, FIGURE II).—It is straight on the bud side and obconoidal opposite the bud. It is 10 to 12 millimeters tall on the bud side and 7 or 8 millimeters opposite the bud. The color is slightly lighter than the internode before exposure to the sun, but turns red with exposure. There are 3 to 4 rows of root primordia, but the rows are not well-defined. The primordia are very light in color with dark centers.

*Leaf scar* (3, FIGURE II).—The leaf scar sometimes protrudes slightly under the bud. It is slightly oblique and tilts under the bud.

*Epidermal cells* (FIGURE VI).—The pattern of the stem epidermal cells is basically Artschwager's type 1 wherein the small cell groups each consist of one cork and one silica cell, the groups occurring singly and alternating with long cells. In perhaps 5 to 10% of the small cell groups there are 2 cork cells associated with one silica cell (type 7). This combination would be designated type 1 + 7. There are occasional pointed cork cells. Small cell groups are rather numerous, averaging approximately 974 per square millimeter. The long cells average about 13.5 microns in width. Stomata are present, averaging about 6 or 7 per square millimeter.

*Stem buds*

*General characteristics.*—The buds (2, FIGURE II) are usually inserted at the leaf scar. The tips extend to the lower edge of the growth ring or less. Buds are not protruding nor overly prominent and have an average size of about 9½ millimeters wide by 9 tall. The prophyll (FIGURE III) is round to ovate with round-pointed tip.

*Wings of the prophyll* (9, FIGURE III).—The wing is broad and is attached above the middle of the prophyll which occasionally extends to the upper edge of the growth ring. The apex is broad, and there is often a notch, which is sometimes toothed, between the lateral halves of the wing.

*Pubescence.*—In general, the pubescence is only moderately conspicuous and this tends to consist of peripheral groups 1, 2, 4, 18, and sometimes 16, 19, and 26. Groups 13 and 14 are also present and may be conspicuous in some buds.

*The leaf*

*The blade.*—The blades are spreading in habit. The color is dark green against which (on the ventral surface) the near-white mid-ribs stand out strikingly. The larger leaves on each stalk are 6.1 to 7.8 centimeters in width, averaging 6.9, and are 126 to 142 centimeters long, averaging 136. The ratio of the length of the blade to the width thereof averages 19.6.

*The sheath.*—The sheaths have an average length of approximately 24 centimeters. As the sheaths grow older the upper ends tend to fall away from the stalks at an angle, exposing portions of the stalks, but the lower ends remain attached until near maturity of the cane when a moderate number drop off completely. The sheaths which adhere are easily pulled off. The dorsal field of pubescence (hair group 57) is about 12 to 15 centimeters long. It begins with a narrow point not far below the dewlaps and broadens to 2 centimeters or more near the middle of the sheath. Group 60 is also present near the margins, and the two groups may coalesce near the middle of the sheath. The hairs are rather long, and they are usually deciduous on mature sheaths.

*Dewlaps* (11, FIGURE 4).—The color of the dewlap varies from about 14–L–1 to 15–L–1 in the plates of Maerz and Paul. The outer surface is moderately covered with wax. The whole outer surface is sparsely covered with group 58 hairs. Group 52 hairs cover about half the inner surface sparsely. This group does not continue across the midrib. Groups 51, 55, and 63 are also present.

*Auricles.*—The outer auricle (12, FIGURE IV) is transitional in shape; the inner auricle (10, FIGURE IV) is small deltoid to short calcarate and varies from about 5 to 10 millimeters in height. There are tufts of hairs on the outer auricle and on the inner margin of the inner auricle.

*Ligules* (FIGURE V).—The ligule is broad crescent-shaped with lozenge and is about 5 millimeters tall in the middle. The marginal cilia (group 61) are irregular in length, but average ½ to ⅔ millimeter in the middle and are shorter on each side.

*Inflorescence.*—This new variety has flowered only once in Florida and that sparingly in a planting on sandy soil only.

Important characteristics which, in combination, help to distinguish this new variety of sugar cane from all other known varieties are:

(1) Medium early maturity.

(2) Very high sucrose content for late harvest.

(3) Ability to grow back vigorously after freezing of above-ground parts.

(4) Susceptibility to mosaic disease when inoculated by artificial means.

(5) Moderate susceptibility to the ratoon stunting disease virus.

(6) Relative resistance to brown stripe disease.

(7) Relative resistance to pokkah boeng.

(8) Stalks nearly circular in cross-section, averaging 32.2 x 33.1 millimeters in diameter in the middles of the stalks.

(9) Low percent fiber in the stalks.

(10) Shallow bud furrows occasionally occur on older internodes.

(11) Growth ring 1 to 2 millimeters high.

(12) There are 3 or 4 rows of root primordia.

(13) The stem epidermal pattern is type 1 + 7 in Artschwager's terminology.

(14) Small cell groups in the stem epidermis average about 974 per square millimeter.

(15) Stomata present in the stem epidermis, averaging 6 or 7 per square millimeter.

(16) Stem buds extend to the lower edge of the growth ring, or less.

(17) The prophyll of the stem bud is round to ovate in shape.

(18) The wing is inserted above the middle of the prophyll.

(19) The blades of the leaves are spreading in habit.

(20) The upper ends of the older leaf sheaths fall away from the stalk at an angle, but remain attached at the base until much later.

(21) The mature leaf sheaths are either self-shedding or are easily pulled off.

(22) The dorsal field of pubescence (group 57) on the leaf sheath is approximately 12 to 15 centimeters long and consists of rather long hairs which are mostly deciduous on mature sheaths. Group 60 is also present near the margin.

(23) Group 52 hairs cover about half the inner surface of the dewlap sparsely and do not extend across the midrib.

(24) The outer auricle is transitional in shape.

(25) The inner auricle is small deltoid to short calcarate in shape.

(26) The ligule is broad crescent-shaped with lozenge.

(27) The marginal cilia of the ligule are irregular in length, but average ½ to ⅔ millimeter on the middle part of the ligule.

(28) Flowering has occurred very sparingly in Florida.

What is claimed is:

The new and distinct variety of sugar cane herein shown and described, identified by the combination of the characteristics enumerated above.

No references cited.

ABRAHAM G. STONE, *Primary Examiner.*

R. E. BAGWILL, *Assistant Examiner.*